(12) United States Patent
Friedl et al.

(10) Patent No.: US 7,695,734 B2
(45) Date of Patent: Apr. 13, 2010

(54) EXTENDED RELEASE TABLET FORMULATION CONTAINING PRAMIPEXOLE OR A PHARMACEUTICALLY ACCEPTABLE SALT THEREOF

(75) Inventors: Thomas Friedl, Ochsenhausen (DE); Wolfram Eisenreich, Ulm (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 988 days.

(21) Appl. No.: 11/202,713

(22) Filed: Aug. 12, 2005

(65) Prior Publication Data

US 2006/0198887 A1    Sep. 7, 2006

(30) Foreign Application Priority Data

Aug. 13, 2004   (EP)   ................... 04019248

(51) Int. Cl.
*A61K 9/22*   (2006.01)
*A61K 9/16*   (2006.01)
*A01N 43/78*   (2006.01)
*A61N 31/425*   (2006.01)

(52) U.S. Cl. ............... 424/468; 424/490; 424/494; 514/367

(58) Field of Classification Search ......... 424/468, 424/490, 494; 514/367
See application file for complete search history.

(56) References Cited

U.S. PATENT DOCUMENTS

| | | | |
|---|---|---|---|
| 2,887,440 A | 5/1959 | Greminger, Jr. et al. | |
| 3,065,143 A | 11/1962 | Christenson et al. | |
| 3,458,622 A | 7/1969 | Hill | |
| 3,845,770 A | 11/1974 | Theeuwes et al. | |
| 4,036,948 A | 7/1977 | Kitamori et al. | |
| 4,140,755 A | 2/1979 | Sheth et al. | |
| 4,167,558 A | 9/1979 | Sheth et al. | |
| 4,389,393 A | 6/1983 | Schor et al. | |
| 4,424,235 A | 1/1984 | Sheth et al. | |
| 4,656,027 A | 4/1987 | Sjöovist | |
| 4,709,712 A | 12/1987 | Bordovsky et al. | |
| 4,731,374 A | 3/1988 | Griss et al. | |
| 4,738,851 A | 4/1988 | Schoenwald et al. | |
| 4,886,812 A | 12/1989 | Griss et al. | |
| 4,968,508 A | 11/1990 | Oren et al. | |
| 5,007,790 A | 4/1991 | Shell | |
| 5,026,559 A * | 6/1991 | Eichel et al. ............. 424/458 |

(Continued)

FOREIGN PATENT DOCUMENTS

CA      1263653      12/1989

(Continued)

OTHER PUBLICATIONS

Abstract taken from AIChE 2006 Spring National Meeting Preliminary Program. Authors: Toson et al. Found at http://aiche.confex.com/aiche/s06/preliminaryprogram/abstract_33412.htm.*

(Continued)

*Primary Examiner*—Anne Marie Grunberg
*Assistant Examiner*—Tracey Simmons Willis
(74) *Attorney, Agent, or Firm*—Michael P. Morris; Mary-Ellen M. Devlin; Philip I. Datlow (57) ABSTRACT

An extended release tablet formulation comprising pramipexole or a pharmaceutically acceptable salt thereof in a matrix comprising at least one water swelling polymer other than pregelatinized starch.

31 Claims, 3 Drawing Sheets

U.S. PATENT DOCUMENTS

| | | | |
|---|---|---|---|
| 5,078,991 A | 1/1992 | Birtwistle et al. | |
| 5,133,974 A * | 7/1992 | Paradissis et al. | 424/480 |
| 5,273,975 A | 12/1993 | Moon et al. | |
| 5,431,920 A | 7/1995 | Bechard | |
| 5,458,887 A | 10/1995 | Chen et al. | |
| 5,472,712 A | 12/1995 | Oshlack et al. | |
| 5,656,296 A | 8/1997 | Khan et al. | |
| 5,731,338 A | 3/1998 | Acharya | |
| 6,056,977 A | 5/2000 | Bhagwat et al. | |
| 6,126,959 A | 10/2000 | Levine et al. | |
| 6,197,339 B1 | 3/2001 | Ju | |
| 6,221,396 B1 | 4/2001 | Chao et al. | |
| 6,248,358 B1 | 6/2001 | Bologna et al. | |
| 6,277,875 B1 | 8/2001 | Holman | |
| 6,340,475 B2 | 1/2002 | Shell et al. | |
| 6,451,343 B1 | 9/2002 | Glinecke et al. | |
| 6,467,637 B2 | 10/2002 | Riga | |
| 6,558,701 B2 | 5/2003 | Bartholomaeus et al. | |
| 6,624,200 B2 | 9/2003 | Bologna et al. | |
| 6,667,060 B1 | 12/2003 | Vandecruys et al. | |
| 6,727,367 B2 | 4/2004 | Pospisilik | |
| 7,153,845 B2 | 12/2006 | Levine et al. | |
| 2002/0010216 A1 | 1/2002 | Rogosky et al. | |
| 2002/0015735 A1 | 2/2002 | Hedden et al. | |
| 2002/0103240 A1 | 8/2002 | Pospisilik | |
| 2002/0114831 A1 | 8/2002 | Norden et al. | |
| 2002/0132850 A1 | 9/2002 | Bartholomaeus et al. | |
| 2003/0077297 A1 * | 4/2003 | Chen et al. | 424/400 |
| 2003/0133982 A1 | 7/2003 | Heimlich et al. | |
| 2003/0180352 A1 | 9/2003 | Patel et al. | |
| 2004/0068119 A1 | 4/2004 | Pospisilik | |
| 2004/0122104 A1 | 6/2004 | Hirsh et al. | |
| 2005/0020589 A1 | 1/2005 | Ganorkar et al. | |
| 2005/0175691 A1 | 8/2005 | Lee et al. | |
| 2005/0226926 A1 | 10/2005 | Amidon et al. | |
| 2006/0051417 A1 | 3/2006 | Friedl et al. | |
| 2006/0051419 A1 | 3/2006 | Friedl et al. | |
| 2006/0198887 A1 | 9/2006 | Friedl et al. | |
| 2007/0196481 A1 | 8/2007 | Amidon et al. | |
| 2008/0031945 A1 | 2/2008 | Eisenreich et al. | |
| 2009/0041844 A1 | 2/2009 | Friedl et al. | |
| 2009/0098202 A1 | 4/2009 | Friedl et al. | |
| 2009/0130197 A1 | 5/2009 | Friedl et al. | |
| 2009/0143387 A1 | 6/2009 | Amidon et al. | |

FOREIGN PATENT DOCUMENTS

| | | | |
|---|---|---|---|
| CA | 2455585 A1 | 2/2003 | |
| DE | 19906290 | 8/2000 | |
| EP | 0186087 | 7/1986 | |
| EP | 0425154 A1 | 5/1991 | |
| EP | 0661045 A1 | 7/1995 | |
| EP | 0895780 A1 | 2/1999 | |
| EP | 0933079 A1 | 8/1999 | |
| GB | 2097676 | 11/1982 | |
| GB | 2338186 | 12/1999 | |
| WO | 9015058 A1 | 12/1990 | |
| WO | 92/01443 | * | 2/1992 |
| WO | 9704752 A1 | 2/1997 | |
| WO | 9855107 A1 | 12/1998 | |
| WO | 9901121 A1 | 1/1999 | |
| WO | 9909066 A1 | 2/1999 | |
| WO | 9916442 A2 | 4/1999 | |
| WO | 9945924 A1 | 9/1999 | |
| WO | 0010536 A1 | 3/2000 | |
| WO | 0059477 A1 | 10/2000 | |
| WO | 0101973 A2 | 1/2001 | |
| WO | 0110405 A1 | 2/2001 | |
| WO | 0119337 A2 | 3/2001 | |
| WO | 0122820 A1 | 4/2001 | |
| WO | 03013521 A1 | 2/2003 | |
| WO | 03053402 A1 | 7/2003 | |
| WO | 2004010982 A1 | 2/2004 | |
| WO | WO 2004/010997 A1 | 2/2004 | |
| WO | WO 2004/010998 A1 | 2/2004 | |
| WO | WO 2004/010999 A1 | 2/2004 | |
| WO | WO/2004/080440 | * | 9/2004 |
| WO | 2004087175 A1 | 10/2004 | |
| WO | 2006015942 A1 | 2/2006 | |
| WO | 2006015943 A2 | 2/2006 | |
| WO | 2006015944 A2 | 2/2006 | |
| WO | 2006046256 A1 | 5/2006 | |
| WO | 2007002516 A2 | 1/2007 | |
| WO | 2007002518 A1 | 1/2007 | |
| WO | 2007022182 A1 | 2/2007 | |
| WO | 2007054976 A2 | 5/2007 | |
| WO | 2007090881 A2 | 8/2007 | |
| WO | 2007090882 A2 | 8/2007 | |
| WO | 2007090883 A2 | 8/2007 | |
| WO | 2008015162 A1 | 2/2008 | |

OTHER PUBLICATIONS

Scheife, R. T. et al, "Impact of Parkinson's disease and its pharmacologic treatment on quality of life and economic outcomes"; US National Library of Medicine, 2000, XP002314706.

Abstract: Scheife, R. T. et al, "Impact of Parkinson's disease and its pharmacologic treatment on quality of life and economic outcomes", American Journal of Health-System Pharmacy, 2000, vol. 57, Issue 10, pp. 953-962.

The Merck Index; Thirteenth Edition; Merck & Co., Inc., Whitehouse Station, NJ, USA.

Remington Farmacia 1988; Alfonso R. Gennaro; 19a Edition; Panamericana Espana; pp. 2470.

International Search Report (Form PCT/ISA/220) for corresponding PCT/EP2005/053610; date of mailing Sep. 12, 2006.

International Search Report (Form PCT/ISA/220) for corresponding PCT/EP2005/053610; date of mailing Nov. 9, 2006.

International Search Report (Form PCT/ISA/220) for corresponding PCT/EP2005/053609; date of mailing Nov. 7, 2006.

Hubble; Pre-clinical studies of pramipexole: clinical relevance; European Journal of Neurology Suppl.; May 2000; vol. 7; No. Supplement 1; pp. 15-20.

Nur et al.; Captopril Floating and/or Bioadhesive Tablets: Design and Release Kinetics; Drug Development and Industrial Pharmacy; 2000; vol. 26; No. 9; pp. 965-969.

Santus; An in vitro-in viro investigation of oral bioadhesive controlled release furosemide formulations; European Journal of Pharmaceutics and Biopharmaceutics; 1997; vol. 44; pp. 39-52.

Elkheshen et al.; In vitro and in vivo Evaluation of Floating Controlled Release Dosage Forms of Verapamil Hydrochloride; Pharm. Ind.; 2004; vol. 66; No. 11; pp. 1364-1372.

Elkheshen et al.; Per-oral Extended-Release Bioadhesive Tablet Formulation of Verapamil HC1; Bollettino Chimico Farmaceutico, Societa Editoriale Farmaceutica, Milano, 2002; vol. 142; No. 5; pp. 226-231.

Biglan et al.; A review of pramipexole and its clinical utility in Parkinson's disease; Expert Opinion on Pharmacotherapy; 2002; vol. 3; No. 2; pp. 197-210.

Colosimo et al.; Motor fluctuations in Parkinson's disease: pathophysiology and treatment; European Journal of Neurology; 1999; vol. 6; No. 1; pp. 1-21.

Dooley et al.; Pramipexole: A Review of its Use in the Management of Early and Advanced Parkinson's Disease; Drugs & Aging; 1998; vol. 12; No. 6; pp. 495-514.

Hiestand et al.; Indices of Tableting Performance; Powder Technology; 1984; vol. 38; pp. 145-159.

Hiestand et al.; Tablet bond. II. Experimental check of model; International Journal of Pharmaceutics; 1991; vol. 67; pp. 231-246.

Hubble et al.; Pramipexole in Patients with Early Parkinson's Disease; Clinical Neuropharmacology; vol. 18; No. 4; pp. 338-347.

Wright et al.; Steady-State Pharmacokinetic Properties of Pramipexole in Healthy Volunteers; Journal of Clinical Pharmacology; 1997; vol. 37; pp. 520-525.

USP 24th Edition; 2000; pp. 1941-1943.
Physicians' Desk Reference; 37th Edition; 2003; pp. 2768-2772.
British National Formulary; 41st ed.; 2001; 196.
Forbes et al.; Progress in Neurology and Psychiatry; vol. 7; No. 2; pp. 10-14.
Lemke; Effect of Reboxetine on Depression in Parkinson's Disease in Patients; Journal of Clinical Psychiatry; 2002; vol. 63; No. 4; pp. 300-304.
Mierau et al.; Pramipexole binding and activation of cloned and expressed dopamine D2, D3 and D4 receptors; European Journal of Pharmacology Molecular Pharmacology Section 290; 1995; pp. 29-36.
Mierau; Pramipexole: A Dopamine-Receptor Agonist for Treatment of Parkinson's Disease; Clinical Neuropharmacology; vol. 18; Supp 1; 1995 Raven Press; pp. S195-S206.
International Preliminary Report on Patentability, Form PCT/IB/373, for corresponding PCT/EP2005/053602.
Non-final Office Action dated Oct. 13, 2006 from U.S. Appl. No. 10/626,275, filed Jul. 24, 2003; Lee et al.
Response to Restriction Requirement dated Mar. 12, 2007 from U.S. Appl. No. 10/626,275, filed Jul. 24, 2003; Lee et al.
Non-final Office Action dated Jun. 11, 2007 from U.S. Appl. No. 10/626,275, filed Jul. 24, 2003; Lee et al.
Amendment dated Dec. 7, 2007 from U.S. Appl. No. 10/626,275, filed Jul. 24, 2003; Lee et al.
Non-final Office Action dated May 29, 2008 from U.S. Appl. No. 10/626,275, filed Jul. 24, 2003; Lee et al.
Amendment and Terminal Disclaimer dated Nov. 26, 2008 from U.S. Appl. No. 10/626,275, filed Jul. 24, 2003; Lee et al.
Interview Summary Form dated Dec. 3, 2008 from U.S. Appl. No. 10/626,275, filed Jul. 24, 2003; Lee et al.
Final Office Action dated Feb. 19, 2009 from U.S. Appl. No. 10/626,275, filed Jul. 24, 2003; Lee et al.
Non-final Office Action dated Sep. 4, 2009 from U.S. Appl. No. 10/626,166, filed Jul. 23, 2003; Amidon et al.
Oct. 5, 2009 Response to Request for Information from U.S. Appl. No. 10/626,166, filed Jul. 24, 2003; Amidon et al.
Non-final Office Action dated Nov. 12, 2009 from U.S. Appl. No. 10/626,275, filed Jul. 24, 2003; Lee et al.
Perez-Marcos et al.; Release of propranolol hydrochloride from matrix tablets containing hydroxypropylmethylcellulose K4M and carbopol 974; International Journal of Pharmaceutics; 1994; vol. 111; pp. 251-259.
Franz et al.; In Vitro Evaluation of a Mixed Polymeric Sustained Release Matrix Using Response Surface Methodology; Journal of Controlled Release; 1987; vol. 5; pp. 159-172.
Bonferoni et al.; Rheological behaviour of hydrophilic polymers and drug release from erodible matrices; Journal of Controlled Release; 1992; vol. 18; pp. 205-212.
Abdallah et al.; Preparation and evaluation of metformin hydrochloride controlled-release tablets; STP Pharma; 1988; vol. 4; pp. 15-20.
Huang et al.; Studies on Drug Release from a Carbomer Tablet Matrix; Drug Development and Industrial Pharmacy; 1995; vol. 21; No. 13; pp. 1487-1501.
Gupta et al.; Hydrogels: from controlled release to pH-responsive drug delivery; Drug Discovery Today; May 2002; vol. 7; No. 10; pp. 569-579.
Li et al.; Effect of HPMC and Carbopol on the release and floating properties of Gastric Floating Drug Delivery System using factorial design; 2003; International Journal of Pharmaceutics; vol. 253; pp. 13-22.
Huber et al.; Utilization of Hydrophilic Gums for the Control of Drug Release from Tablet Formulations I. Disintegration and Dissolution Behavior; Journal of Pharmaceutical Sciences; Sep. 1966; vol. 55; No. 9; pp. 974-976.
Perez-Marcos et al.; Influence of pH on the Release of Propranolol Hydrochloride from Matrices Containing Hydroxypropylmethylcellulose K4M and Carbopol 974; Journal of Pharmaceutical Sciences; Mar. 1996; vol. 85; No. 3; pp. 330-334.
Huber et al.; Utilization of Hydrophilic Gums for the Control of Drug Substance Release form Tablet Formulations II. Influence of Tablet Hardness and Density on Dissolution Behavior; Journal of Pharmaceutical Sciences, 1968; vol. 57; pp. 164-166.

* cited by examiner

EXTENDED RELEASE TABLET FORMULATION CONTAINING PRAMIPEXOLE OR A PHARMACEUTICALLY ACCEPTABLE SALT THEREOF

RELATED APPLICATIONS

This application claims priority to European Application No. 04019248.6 filed Aug. 13, 2004, which is hereby incorporated by reference in its entirety.

FIELD OF THE INVENTION

The present invention is directed to an extended release tablet formulation containing pramipexole or a pharmaceutically acceptable salt thereof, a method for manufacturing the same, and use thereof.

BACKGROUND OF THE INVENTION

Pramipexole is a known dopamine D2 receptor agonist. It is structurally different from the ergot-derived drugs, e.g., bromocriptine or pergolide. It is also pharmacologically unique in that it is a full agonist and has receptor selectivity for the dopamine D2 family of dopamine receptors.

Pramipexole is designated chemically as (S)-2-amino-4,5,6,7-tetrahydro-6-(propylamino)benzothiazole and has the molecular formula $C_{10}H_{17}N_3S$ and a relative molecular mass of 211.33. The chemical formula is as follows:

The salt form commonly used is pramipexole dihydrochloride monohydrate (molecular formula $C_{10}H_{21}Cl_2N_3OS$; relative molecular mass 302.27). Pramipexole dihydrochloride monohydrate is a white to off-white, tasteless, crystalline powder. Melting occurs in the range of 296° C. to 301° C., with decomposition. Pramipexole is a chiral compound with one chiral center. Pure (S)-enantiomer is obtained from the synthetic process by chiral recrystallization of one of the intermediates during synthesis.

Pramipexole dihydrochloride monohydrate is a highly soluble compound. Water solubility is more than 20 mg/mL and solubility in buffer media is generally above 10 mg/mL between pH 2 and pH 7.4. Pramipexole dihydrochloride monohydrate is not hygroscopic, and has a highly crystalline nature. Under milling, the crystal modification (monohydrate) does not change. Pramipexole is very stable in the solid state, yet in solution it is light sensitive.

Pramipexole immediate release (IR) tablets were first authorized in the USA in 1997, followed over the course of the next years by marketing authorizations in the European Union (EU), Switzerland, Canada, and South America as well as in countries in Eastern Europe, the Near East, and Asia.

Pramipexole IR tablets are indicated in the EU and US for the treatment of signs and symptoms of either early Parkinson's Disease or advanced Parkinson's Disease in combination with levodopa. The IR tablets have to be taken 3 times a day.

From the pharmacokinetic point of view, pramipexole IR tablets are rapidly and completely absorbed following oral administration. The absolute bioavailability is greater than 90% and the maximum plasma concentration occurs within 1 to 3 hours. The rate of absorption is reduced by food intake but not the overall extent of absorption. Pramipexole shows linear kinetics and a relatively small inter-patient variation of plasma levels. The elimination half-life ($t_{1/2}$[h]) varies from 8 hours in the young to 12 hours in the elderly.

As is commonly known, modified release of active ingredient(s) allows simplification of the patient's administration scheme by reducing the amount of recommended daily intakes, improves patient's compliance, and attenuates adverse events, e.g., related to high plasma peaks. Modified release pharmaceutical preparations regulate the release of the incorporated active ingredient or ingredients over time and comprise formulations with a controlled, a prolonged, a sustained, a delayed, a slow or an extended release, so they accomplish therapeutic or convenience objectives not offered by conventional dosage forms such as solutions or promptly dissolving dosage forms.

A modified or extended release of active ingredient(s) from a pharmaceutical preparation may be accomplished by homogeneously embedding the active ingredient(s) in a hydrophilic matrix, being a soluble, partially soluble or insoluble network of viscous, hydrophilic polymers, held together by physical or chemical entanglements, by ionic or crystalline interactions, by complex formation, by hydrogen bonds or van der Waals forces. The hydrophilic matrix swells upon contact with water, thereby creating a protective gel layer from which the active ingredient(s) are slowly, gradually, continuously released in time either by diffusion through the polymeric network, by erosion of the gel layer, by dissolution of the polymer, or by a combination of these release mechanisms.

However, it has proved difficult to formulate a tablet having a suitable combination of modified, extended or sustained-release and handling properties, where the drug is one having relatively high solubility, as in the case of pramipexole dihydrochloride.

There are a number of approaches described in prior art to provide sustained release tablet compositions of pramipexole.

WO 2004/010997 describes a sustained-release pharmaceutical composition in a form of an orally deliverable tablet comprising a water-soluble salt of pramipexole, dispersed in a matrix comprising a hydrophilic polymer and a starch having a tensile strength of at least about 0.15 kN cm$^{-2}$, preferably at least about 0.175 kN cm$^{-2}$, and more preferably at least about 0.2 kN cm$^{-2}$, at a solid fraction representative of the tablet. The disclosure thereof is concentrated to provide a composition with sufficient hardness yield during a high-speed tabletting operation, in particular to resist erosion during application of a coating layer. According to a preferred embodiment it is provided a pharmaceutical composition in a form of an orally deliverable tablet having a core comprising pramipexole dihydrochloride monohydrate in an amount of about 0.375, 0.75, 1.5, 3, or 4.5 mg, dispersed in a matrix comprising (a) HPMC type 2208 in an amount of about 35% to about 50% by weight of the tablet and (b) a pregelatinized starch having a tensile strength of at least about 0.15 kN cm$^{-2}$ at a solid fraction of 0.8, in an amount of about 45% to about 65% by weight of the tablet; the core being substantially enclosed in a coating that constitutes about 2% to about 7% of the weight of the tablet, the coating comprising an ethyl cellulose-based hydrophobic or water-insoluble component and an HPMC-based pore-forming component in an amount of about 10% to about 40% by weight of the ethyl cellulose-based component.

Furthermore, WO 2004/010999 discloses an orally deliverable pharmaceutical composition comprising a therapeutically effective amount of pramipexole or a pharmaceutically acceptable salt thereof and at least one pharmaceutically acceptable excipient, the composition exhibiting at least one of (a) an in vitro release profile wherein on average no more than about 20% of the pramipexole is dissolved within 2 hours after placement of the composition in a standard dissolution test; and (b) an in vivo pramipexole absorption profile following single dose oral administration to healthy adult humans wherein the time to reach a mean of 20% absorption is greater than about 2 hours and/or the time to reach a mean of 40% absorption is greater than about 4 hours. However, in practical use, it appears that any formulation having an extended or controlled release profile designed for a once daily application would meet the above requirements for which a general teaching how to adjust such a profile is missing.

It is an object of the present invention to provide a controlled release tablet composition of pramipexole or a pharmaceutically acceptable salt thereof that is suitable for once-daily oral administration. It is a further object to provide a tablet composition comprising pramipexole or a pharmaceutically acceptable salt thereof that provides a day-long therapeutic effect and will allow patients to treat their symptoms with a single daily dose, which makes it possible to adjust the release profile of the active ingredient according to a selected release profile dependent or independent from the pH values. Furthermore a method of manufacturing the tablet formulation shall be provided.

DESCRIPTION OF THE INVENTION

Surprisingly, it has been found that pramipexole or a pharmaceutically acceptable salt thereof may be used in formulations as once daily extended (or slow) release tablets and two alternative formulation principles allow different release rate types dependent or independent from the pH value.

The present invention relates to an extended release tablet formulation comprising pramipexole or a pharmaceutically acceptable salt thereof in a matrix comprising at least one water swelling polymer other than pregelatinized starch.

Preferably the invention relates to an extended release tablet formulation, wherein the matrix comprises at least two water swelling polymers other than pregelatinized starch, and wherein at least one of the at least two polymers is an anionic polymer.

Also preferred is an extended release tablet formulation, wherein the anionic polymer is selected from the group of optionally crosslinked acrylic acid polymers, methacrylic acid polymers, alginates, and carboxymethyl cellulose.

Also preferred is an extended release tablet formulation, wherein the anionic polymer is an optionally crosslinked acrylic acid polymer, and wherein the content of the optionally crosslinked acrylic acid polymer in the matrix is from about 0.25 wt.-% to about 25 wt.-%, and preferably from about 0.5 wt.-% to about 15 wt.-%, and preferably from about 1 wt.-% to about 10 wt.-%.

Also preferred is an extended release tablet formulation, wherein at least one of the at least two polymers is a substantially neutral polymer other than pregelatinized starch.

Also preferred is an extended release tablet formulation, wherein the substantially neutral polymer is selected from hydroxypropyl cellulose and hydroxypropyl methyl cellulose.

Particularly preferred is an extended release tablet formulation, wherein the substantially neutral polymer is hydroxypropyl methyl cellulose, and wherein the content of hydroxypropyl methyl cellulose in the matrix is from about 10 wt.-% to about 75 wt.-% and preferably from about 25 wt.-% to about 65 wt.-%.

Particularly preferred is an extended release tablet formulation, wherein the matrix comprises about:

(a) 0.05 to 5 wt.-% of pramipexole or a salt thereof;

(b) 0.25 to 25 wt.-% of anionic water swelling polymer(s);

(c) 10 to 75 wt.-% of neutral water swelling polymer(s); and (d) further excipients to 100 wt.-%

Particularly preferred is an extended release tablet formulation consisting of pramipexole dihydrochloride monohydrate, Hypromellose 2208, corn starch, Carbomer 941, colloidal silicon dioxide, and magnesium stearate.

A preferred embodiment of the present invention relates to an extended release tablet formulation comprising pramipexole or a pharmaceutically acceptable salt thereof in a matrix comprising:

(a) at least one water swelling polymer other than pregelatinized starch and optionally excipients, the resulting tablet providing a pH-independent in vitro release characteristic in the range from pH 1 to 7.5, or (b) at least one water swelling anionic polymer and optionally excipients, the resulting tablet providing a pH-dependent release characteristic with a faster release characteristic in the range of pH<4.5, and a slower and further on pH-independent release characteristic in the range from pH 4.5 to 7.5.

Most preferably the present invention relates to a matrix of the extended release tablet formulation comprising at least one water swelling polymer other than pregelatinized starch, preferably a water swelling essentially neutral polymer, a water swelling anionic polymer and optionally excipients, the resulting tablet providing a pH-dependent release characteristic with a faster release characteristic in the range of pH<4.5, and a slower and further on pH-independent release characteristic in the range from pH 4.5 to 7.

The extended release formulations according to the present invention intended for oral administration allow to select and estimate which in vitro release characteristic and timing of a formulation is most suitable to achieve the desired in vivo plasma profiles preferably with a once daily application. Therefore, a formulation principle with several variants has been developed for a single unit matrix tablet, i.e., formulations having different release rate types are provided and a different pH dependency is available. These alternative formulations are beneficial to patients as the extended release drug delivery will allow patients to treat their symptoms with a single daily dose, thereby increasing patient convenience and compliance.

The term "in vitro release characteristic" as used hereinbefore or hereinafter is directed to a release characteristic as obtained in a kind of normally used liquid medium for in vitro experiments wherein the release of active ingredient from the extended release formulation can occur, i.e., for example, in in vitro dissolution media, but also in body fluids or simulated body fluids, more in particular in the gastrointestinal fluids.

In the frame of the present invention the term "extended" release should be understood in contrast to an immediate release, the active ingredient is gradually, continuously liberated over time, sometimes slower or faster, dependent or independent from the pH value. In particular, the term indicates that the formulation does not release the full dose of the active ingredient immediately after oral dosing and that the formulation allows a reduction in dosage frequency, following the definition for extended release, interchangeable with slow release. A slow or extended release, used synonymously with prolonged action, sustained release, or modified release, dosage form is a dosage form that allows a reduction in dosing frequency or a significant increase in patient compliance or therapeutic performance as compared to that presented as a conventional dosage form (e.g., as a solution or an immediate drug-releasing, conventional solid dosage form).

A release characteristic which is pH-independent indicates that the release characteristic is virtually the same in different pH media.

According to the teaching of the present invention, extended release tablet formulations are provided with different in vitro release profiles.

The extended release tablets of the present invention are believed to apply a swelling and partly eroding polymer matrix. Based on the assumed mechanisms, the release profile may roughly follow a square root of time to exponential in vitro release characteristic. Depending on the particular embodiment formulation a) is widely independent from the pH value in the range from pH 1 to 7.5, and formulation b) is faster in simulated gastric juice having a pH<4.5 but are independent from the pH value in the range from 4.5 to 7.5. A faster release in simulated gastric juice versus slower release in the intestinal fluid can be advantageous in cases where a loading dose effect from the dosage form is desired, whereas a widely pH independent release profile can be advantageous to reduce the risk of dose dumping and food effects.

According to the present invention under "formulation a)" is understood the tablet formulation wherein the matrix comprises the composition as above-defined under a) and under "formulation b)" is understood the tablet formulation wherein the matrix comprises the composition as above-defined under b).

The water swelling polymer of the present invention represents at least one hydrophilic water swelling polymer constituting the extended release matrix which slowly releases the pramipexole or its salt as active ingredient. The polymer swells upon contact with aqueous fluid following administration, resulting in a viscous, drug release regulating gel layer. The viscosity of the polymer preferably ranges from 150 to 100,000 mPa·s (apparent viscosity of a 2% aqueous solution at 20° C.).

Examples of such polymers are water swelling substantially neutral polymers or water swelling anionic polymers.

The term "water swelling substantially neutral polymers" of the present invention comprises alkyl celluloses such as methyl cellulose; hydroxyalkyl celluloses, for example, hydroxymethyl cellulose, hydroxyethyl cellulose, hydroxypropyl cellulose, and hydroxybutyl cellulose; hydroxyalkyl alkyl celluloses such as hydroxyethyl methyl cellulose and hydroxypropyl methyl cellulose; carboxyalkyl cellulose esters; other natural, semi-synthetic, or synthetic di-, oligo-, and polysaccharides such as galactomannans, tragacanth, agar, guar gum, and polyfructans; methacrylate copolymers; polyvinyl alcohol; polyvinylpyrrolidone, copolymers of polyvinylpyrrolidone with vinyl acetate; combinations of polyvinyl alcohol and polyvinylpyrrolidone; and polyalkylene oxides such as polyethylene oxide and polypropylene oxide and copolymers of ethylene oxide and propylene oxide, preferably cellulose ether derivatives such as hydroxypropyl methyl cellulose and hydroxypropyl cellulose, most preferred hydroxypropyl methyl cellulose.

The term "water swelling anionic polymer" of the present invention comprises acrylic acid polymerisate, methacrylic acid copolymers, alginates, carrageenans, acacia, xanthan gum, chitin derivates such as chitosan, carmellose sodium, and carmellose calcium, preferably acrylic acid polymerisate.

Different viscosity grades of hydroxypropyl cellulose and hydroxypropyl methyl cellulose are commercially available. Hydroxypropyl methyl cellulose (HPMC) preferably used in the present invention has a viscosity grade ranging from about 3,500 mPa·s to about 100,000 mPa·s, in particular ranging from about 4,000 mPa·s to about 20,000 mPa·s and most in particular a viscosity grade of about 6,500 mPa·s to about 15,000 mPa·s (apparent viscosity of a 2% aqueous solution at 20° C.), e.g., hypromellose 2208 or 2206 (DOW, Antwerp, Belgium). HPMC type 2208 contains 19-24% by weight methoxy and 4-12% by weight hydroxypropoxy substituents.

Hydroxypropyl cellulose having a viscosity higher than 1,500 mPa·s (apparent viscosity of a 1% aqueous solution at 20° C.) is preferred, in particular hydroxypropyl cellulose having a viscosity in the range from about 1500 to about 3000 mPa·s, preferably from 4000 to 6500 mPa·s (2% aqueous solutions), e.g., the Klucel series such as Klucel M (Hercules, Wilmington, USA).

Without wishing to be bound by theory, there are believed to exist three main mechanisms by which pramipexole or a salt thereof can be released from a hydrophilic matrix: dissolution, erosion and diffusion. Pramipexole or its salt will be released by the dissolution mechanism when it is homogeneously dispersed in a matrix network of a soluble polymer. The network will gradually dissolve in the gastrointestinal tract, thereby gradually releasing its load. The matrix polymer can also gradually be eroded from the matrix surface, likewise releasing pramipexole or its salt in time. When pramipexole is processed in a matrix made up of an insoluble polymer, it will be released by diffusion: the gastrointestinal fluids penetrate the insoluble, sponge-like matrix and diffuse back out loaded with drug.

Therefore, the water swelling polymers constituting the matrix, particularly in a matrix according to formulation a), mainly provide for the controlled pharmacokinetic release profile of the preparation. Depending on the amount of water swelling polymer(s) processed in the preparation, the release profile can be tuned, i.e., larger amounts of swelling polymer lead to a more pronounced sustained release effect and vice versa. Preferably, the amount of water swelling polymer in the present formulation ranges from about 10 to about 80% by weight.

In addition, when using a combination of polymers, the ratio of the polymers also influences the release profile of the preparation. A combination of different polymers offers the possibility of combining different mechanisms by which pramipexole is released from the matrix. Such combination facilitates control of the pharmacokinetic release profile of the preparation at will. For example, when using one or more water swelling polymers, in particular hydroxypropyl cellulose and hydroxypropyl methyl cellulose, the weight percentage of hydroxypropyl methyl cellulose preferably ranges from 25 to about 62%; the weight percentage of hydroxypropyl cellulose preferably ranges between 0% and about 16%.

Release of pramipexole or a salt thereof from a matrix containing hydroxypropyl cellulose and hydroxypropyl methyl cellulose occurs by a combined set of release mechanisms. Due to the higher solubility of hydroxypropyl methyl cellulose compared with hydroxypropyl cellulose, the former will gradually dissolve and erode from the matrix, whereas the latter will more act as a sponge-like matrix former releasing the active ingredient mainly by diffusion.

The extended release tablet formulation according to formulation a) is pH-independent. Therefore, the disadvantage that food related dose-dumping may be encountered is avoided. The problem of food related dose-dumping in fed patients can be attributed to a lot of factors such as the mechanical forces that are exerted by the stomach on its content and thus on an ingested preparation as well as the different pH regions of the gastrointestinal tract. Since the pH values encountered in the gastrointestinal tract vary not only with the region of the tract, but also with the intake of food, an extended release formulation preferably also has to provide an extended release profile and in particular has to avoid dose-dumping regardless whether the patient is in fasted or fed conditions.

According to the present invention the oral extended release formulation a) retains its pharmacokinetic release profile along its way through the gastrointestinal tract so as to avoid undesirable fluctuations in drug plasma concentrations or complete dose-dumping, in particular avoids dose-dumping in different regions of the gastrointestinal tract.

Beside pramipexole or a salt thereof, and the water swelling polymer(s), the formulation of the present invention may also optionally comprise further excipients, i.e., pharmaceutically acceptable formulating agents, in order to promote the manufacture, compressibility, appearance, and taste of the preparation. These formulating agents comprise, for example, diluents or fillers, glidants, binding agents, granulating agents, anti-caking agents, lubricants, flavors, dyes, and preservatives. Other conventional excipients known in the art can also be included.

The filler may be selected from soluble fillers, for example, sucrose, lactose, in particular lactose monohydrate, trehalose, maltose, mannitol and sorbitol. Different grades of lactose can be used. One type of lactose preferably used in the present invention is lactose monohydrate 200 mesh (DMV, Veghel, The Netherlands). Another lactose monohydrate, lactose monohydrate of the type DCL 11 (DMV, Veghel, The Netherlands), can also preferably be used. The notation DCL refers to "Direct Compression Lactose". The number 11 is a reference number of the manufacturer. In case of a water soluble active ingredient, like the one described in this invention, more preferably water insoluble fillers, such as starch and starch derivates other than pregelatinized starch, e.g., corn starch, potato starch, rice starch or wheat starch, microcrystalline cellulose, dibasic calcium phosphate dihydrate, and anhydrous dibasic calcium phosphate, preferably corn starch, can be used in addition or instead of the water soluble fillers. The total weight percentage of filler ranges between about 5% and about 75% by weight.

A glidant can be used to improve powder flow properties prior to and during tabletting and to reduce caking. Suitable glidants include colloidal silicon dioxide, magnesium trisilicate, powdered cellulose, talc, tribasic calcium phosphate and the like. Colloidal silicon dioxide is preferably included as a glidant in an amount up to about 2%, preferably about 0.2% to about 0.8%, by weight of the tablet.

A lubricant can be used to enhance release of a tablet from apparatus on which it is formed, for example by preventing adherence to the face of an upper punch ("picking") or lower punch ("sticking"). Suitable lubricants include magnesium stearate, calcium stearate, canola oil, glyceryl palmitostearate, hydrogenated vegetable oil, magnesium oxide, mineral oil, poloxamer, polyethylene glycol, polyvinyl alcohol, sodium benzoate, sodium lauryl sulfate, sodium stearyl fumarate, stearic acid, talc, hydrogenated vegetable oil, zinc stearate and the like. In one embodiment, magnesium stearate is included as a lubricant in an amount of about 0.1% to about 1.5%, preferably about 0.3% to about 1%, by weight of the tablet.

Among the optional formulating agents that further may be comprised in the matrix formulation there may be mentioned agents such as polyvidone; copovidone; starch; acacia; gelatin; seaweed derivatives, e.g., alginic acid, sodium and calcium alginate; cellulose, preferably microcrystalline cellulose, cellulose derivatives, e.g., ethyl cellulose, hydroxypropyl cellulose, and hydroxypropyl methyl cellulose, having useful dry or wet binding and granulating properties; and antiadherents such as talc and magnesium stearate.

According to a preferred embodiment of the present invention the matrix of the extended release tablet formulation of alternative a) comprises or essentially consists of hydroxypropyl methyl cellulose, such as hypromellose, and further excipients. The amount of hydroxypropyl methyl cellulose is preferably in the range from 10 to 75%, particularly preferred from 25 to 65% most preferred from 35 to 55% by weight. The amount of further excipients is preferably in the range from 90 to 25%, particularly preferred from 75 to 35%, most preferred from 65 to 45% by weight.

The expression "consisting essentially" is understood in the sense that it does not in principle exclude the presence, in addition to the mandatory components mentioned, of other components, the presence of which does not affect the essential nature of the formulation.

In some embodiments of the present invention it is provided a pH-dependent release profile, the release of pramipexole or its salt from the tablet and subsequent the absorption into the blood stream can vary during the passage of the dosage form along the gastrointestinal tract. Thus, formulation b) provides a pH-dependent release characteristic wherein the release characteristic in the range of pH<4.5 is faster and a slower and further on pH-independent release characteristic in the range from $4.5 \leq pH \leq 7.5$.

The above details for the water swelling polymer and selection and type of optional excipients may apply to formulation b), too.

Moreover, an anionic water swelling polymer, preferably an acrylic acid polymerisate is mandatorily present in formulation b), which is preferably selected from carbomer or CARBOPOL® series, known acrylic acid polymerisates having high molecular weights. Particularly preferred are, for example, carbomer 941 (CARBOPOL® 71 G, CARBOPOL® 971) and carbomer 934 (CARBOPOL® 974). The acrylic acid polymerisate is preferably present in the range of 0.25 to 25% by weight, particularly preferred 0.5 to 15% by weight, most preferred 1 to 10% by weight. The pH dependency of formulation b) results from the presence of an anionic water swelling polymer, particularly preferred from the presence of acrylic acid polymerisate which intends to swell in a greater extent in the acid pH range above pH 4.5 and in the alkaline pH range.

An increasing amount of acrylic acid leads to a decrease of the release rate. Therefore, adjusting the amount of acrylic acid polymerisate makes it possible to further tune the dissolution profiles as desired. To adjust the amount of acrylic acid polymerisate in the preferred range from 0.25 to 25% by weight provides the further advantage that the desired, resp. matching, dissolution profiles can be adjusted, resp. maintained, for a variety of formulations composed of different amounts and/or types of gel-forming agents, water swelling polymers, fillers, and dry binders.

According to a preferred embodiment of the present invention the matrix of the extended release tablet formulation comprises or essentially consists of hydroxypropyl methyl cellulose, acrylic acid polymerisate and further excipients. The amount of hydroxypropyl methyl cellulose is preferably in the range from 10 to 75%, particularly preferred from 25 to 65%, most preferred from 35 to 55% by weight. The amount of acrylic acid polymerisate is preferably as abovementioned. The amount of additional excipients is preferably in the range from 90 to 25% particularly preferred from 75 to 35%, most preferred from 65 to 45% by weight. Optionally carboxymethyl cellulose sodium may additionally be present preferably in the range from 5 to 50%, particularly preferred from 10 to 40%, most preferred from 15 to 30% by weight.

As active ingredient, pramipexole or a pharmaceutically acceptable salt thereof, may be present in any amount suitable for the desired treatment of a patient. A preferred salt of pramipexole is the dihydrochloride salt, most preferably in the form of the monohydrate. Usual amounts are from about 0.1 to about 5 mg of pramipexole salt. According to a particularly preferred embodiment e.g., 0.750 mg of pramipexole dihydrochloride monohydrate, corresponding to 0.524 mg of anhydrous base, is used in the extended release tablet formulation according to the present invention. However, any other amount of active ingredient suitable for treatment may be used with the only proviso that the amount of pramipexole or salt is sufficient to provide a daily dose in one to a small plurality, for example one to about 4, of tablets to be administered at one time. Preferably the full daily dose is delivered in a single tablet. An amount of pramipexole salt, expressed as pramipexole dihydrochloride monohydrate equivalent, of about 0.1 to about 10 mg per tablet, or about 0.05% to about 5% by weight of the composition, will generally be suitable. Preferably an amount of about 0.2 to about 6 mg, more preferably an amount of about 0.3 to about 5 mg, per tablet is present. Specific dosage amounts per tablet, e.g., include 0.375, 0.5, 0.75, 1.0, 1.5, 3.0, and 4.5 mg of pramipexole dihydrochloride monohydrate. The amount that constitutes a therapeutically effective amount varies according to the condition being treated, the severity of the condition, and the patient being treated.

An extended release tablet formulation according to the present invention, has preferably the following composition:
  (a) 0.05 to 5% by weight of pramipexole or a salt thereof;
  (b) 10 to 75% by weight water swelling polymer(s);
  (c) 0 to 25% by weight acrylic acid polymerisate; and
  (d) to 100% by weight of optional further excipient(s).

Therefore, a particularly preferred extended release tablet formulation of the present invention consists of:
  (a) 0.1 to 2% by weight of pramipexole or a salt thereof;
  (b) 25 to 65% by weight of hydroxypropyl methyl cellulose;
  (c) 0 to 40% by weight of carboxymethyl cellulose sodium;
  (d) 0 to 75% by weight of corn starch other than pregelatinized starch;
  (e) 0 to 15% by weight of acrylic polymerisate, preferably carbomer 941; and
  (f) 0.5 to 50% by weight of excipients, preferably selected from the group consisting of colloidal silicon dioxide, magnesium stearate, lactose monohydrate, mannitol, microcrystalline cellulose, dibasic anhydrous calcium phosphate, hydroxypropyl cellulose, povidone, copovidone, talc, macrogols, sodium dodecylsulfate, iron oxides, and titanium dioxide.

According to the present invention starch other than pregelatinized starch, preferably corn starch if present, may impart several functions at the same time such as filler, glidant, and the like. However, it may be preferred to exclude starch completely from the tablet formulation according to the present invention, which may be replaced by one or more of the above-mentioned other excipient(s). Furthermore, a starch having a tensile strength of at least about 0.15 kN cm$^{-2}$ at a solid fraction representative of the tablet as claimed according to WO 2004/010997 is not required according to the present invention.

It is preferred that no coating is present on the tablet formulation according to the present invention. However, the extended release tablet of the invention may comprise a nonfunctional coating. A nonfunctional coating can comprise a polymer component, for example HPMC, optionally with other ingredients, for example, one or more plasticizers, colorants, etc. The term "nonfunctional" in the present context means having no substantial effect on release properties of the tablet, and the coating serves another useful purpose. For example, such a coating can impart a distinctive appearance to the tablet, provide protection against attrition during packaging and transportation, improve ease of swallowing, and/or have other benefits. A nonfunctional coating should be applied in an amount sufficient to provide complete coverage of the tablet. Typically an amount of about 1% to about 10%, more typically an amount of about 2% to about 5%, by weight of the tablet as a whole, is suitable.

The tablets of the present invention can be of any suitable size and shape, for example round, oval, polygonal, or pillow-shaped, and optionally bear nonfunctional surface markings. According to the present invention it is preferred that the extended release tablets are white to off-white and of oval or round, biconvex, shape.

Tablets of the invention can be packaged in a container, accompanied by a package insert providing pertinent information such as, for example, dosage and administration information, contraindications, precautions, drug interactions, and adverse reactions.

The present invention is further directed to the use of the extended release tablet formulation according to the present invention for preparing a medical composition for the treatment of Parkinson's Disease and complications or disorders associated therewith.

Furthermore, the present invention is preferably directed to a method of manufacturing the extended release tablet formulations via a direct compression process comprising the steps of:
  (1) producing an active ingredient trituration wherein the active ingredient is pramipexole or a pharmaceutically acceptable salt thereof by preblending it with a portion of water swelling polymer(s) and/or further excipient(s) in a mixer, wherein pramipexole or the pharmaceutically acceptable salt thereof is milled, preferably peg-milled, prior to use;
  (2) premixing the active ingredient trituration of step (1), the main portion of the water swelling polymer(s) and/or excipients in a mixer to obtain a pre-mixture;
  (3) optionally dry screening the pre-mixture through a screen in order to segregate cohesive particles and to improve content uniformity;
  (4) mixing the pre-mixture of step (2) or (3) in a mixer, optionally by adding remaining excipients to the mixture and continuing mixing; and
  (5) tabletting the final mixture by compressing it on a suitable tablet press to produce matrix tablets.

Therefore, the tablets are manufactured via a direct compression process which applies to both types of pramipexole extended release matrix tablets. To achieve adequate content uniformity in this low drug load formulation, the active ingredient is preferably peg-milled. Preferably the particle size distribution of the peg-milled drug substance, as determined by laser diffractometry using a dry dispensing system, is characterized by particle fraction of 90% (v/v) being smaller than 100 μm, most preferably a particle fraction of 90% (v/v) being smaller than 75 μm in diameter.

Also other processes can be applied to the manufacturing of Pramipexole extended release tablets, like conventional wet granulation and roller compaction. In case of wet granulation preferably Pramipexole is granulated with suitable fillers, like, e.g., starches other than pregelatinized starch, microcrystalline cellulose, lactose monohydrate or anhydrous dibasic calcium phosphate, and wet binding agents, like, e.g., hydroxypropyl methyl cellulose, hydroxypropyl cellulose, povidone, copovidone, and starch paste, leading to a active ingredient concentrate, which after drying and dry screening is mixed with the main fraction of gel forming excipients, like all the above described retarding principles.

In case of roller compaction, or in other words dry granulation, either a premix of Pramipexole with part of the excipients used in the direct compression process, or the complete mixture containing all excipients, is processed through a conventional roller compactor to form ribbons, which are thereafter screened down to granules which are finally mixed with other excipients, like glidants, lubricants and antiadherents.

BRIEF DESCRIPTION OF THE DRAWINGS

Figure 1:
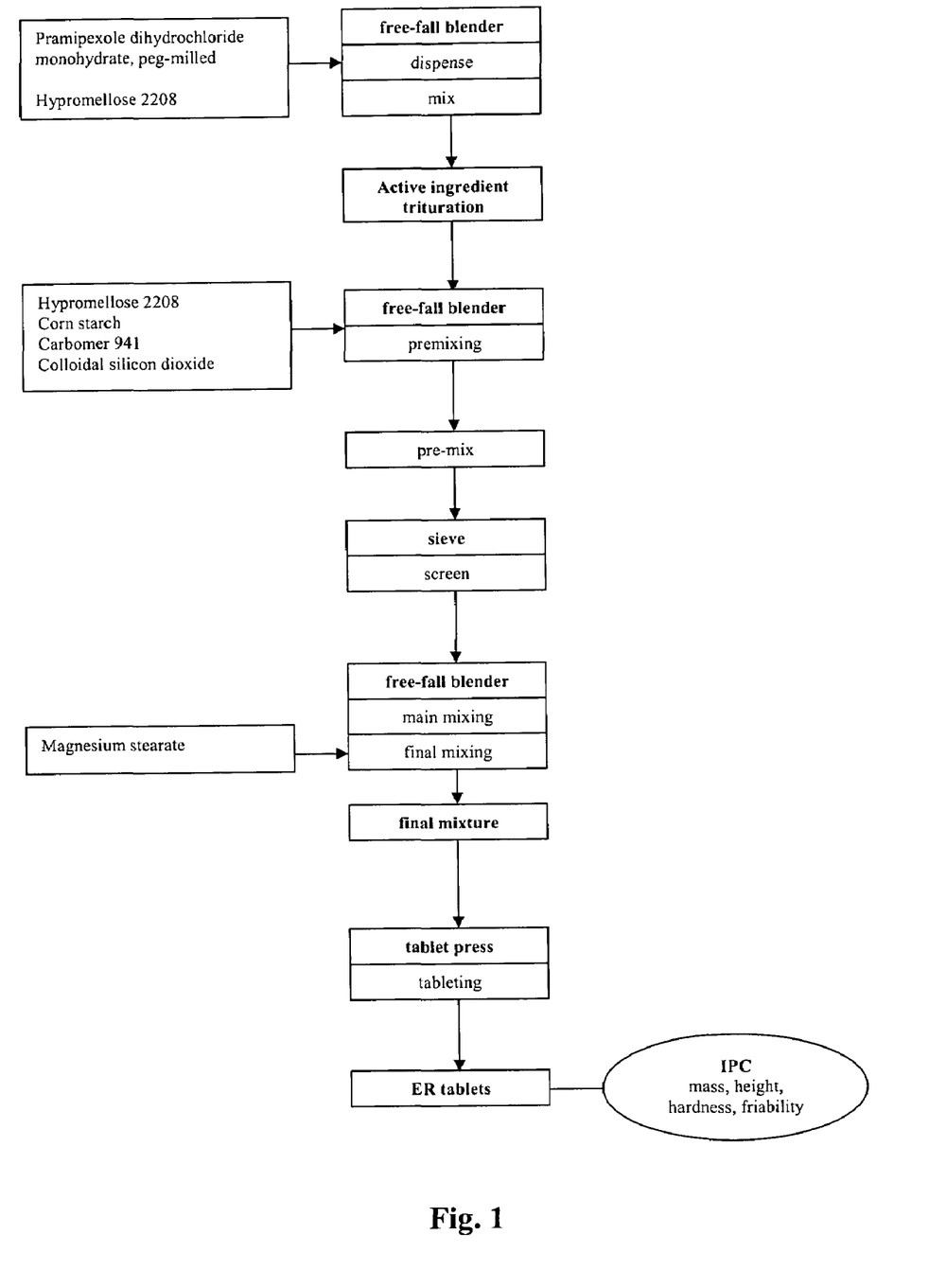
FIG. 1 is a flow diagram illustrating a preferred embodiment of the direct compression manufacturing process according to the present invention.

FIG. 1 illustrates a preferred embodiment of the manufacturing process with reference to a flow diagram wherein the manufacture of the extended release tablets of Examples 1 and 2 are exemplarily shown. FIG. 1 shows the detailed process steps and the in process controls performed.

Process step (1) is directed to the active ingredient trituration, i.e., in the present case a salt of pramipexole, pramipexole dihydrochloride monohydrate, in peg-milled quality, is preblended with a portion of the polymer, in this case hydroxypropyl methyl cellulose, in a commonly known mixer. In the flow chart, a TURBULA® free-fall mixer or blender is used. The mixing time is several minutes, in the present case preferably 10 minutes.

In process step (2) according to the flow chart a premixing is performed, wherein the active ingredient trituration and the main portion of the water swelling polymer(s) and excipients are premixed for several minutes to obtain a pre-mix. In the present case the main portion of hydroxypropyl methyl cellulose (hypromellose), corn starch, carbomer 941 and colloidal silicon dioxide are premixed for 5 minutes in the above-mentioned TURBULA® mixer or blender.

According to the following process step (3) a dry screening may optionally take place. The pre-mixture may be manually screened through a screen, for example a 0.8 mm mesh size screen, in order to segregate cohesive particles and to improve content uniformity.

In the subsequent process step (4) the main mixing step is performed according to which the components are mixed for several minutes, preferably 5 minutes in the TURBULA® mixer after screening. Optionally further excipients may be added at this time, in the flow chart the component magnesium stearate is added to the main mixture, and further mixing for several minutes, e.g., 3 minutes, in the TURBULA® mixer is performed (final mixing) to obtain the final mixture.

Process step (5) of the process according to the present invention is the tabletting. The final mixture is compressed on a suitable tablet press to produce, for example, oblong shaped matrix tablets (ER tablets=extended release tablets). In order to control and maintain the required quality the obtained matrix tablets are subjected to the following in-process controls: tablet mass, hardness, tablet height and friability.

The obtained pramipexole extended release tablets of the present invention may then be filled, for example, into high density polyethylene (HDPE) bottles. The bottles are closed tightly with screw caps and appropriately labeled, whereby all packaging and labeling activities are performed according to cGMP regulations. Alternatively, a blister type packaging can be used, e.g., using aluminum/aluminum foil blisters.

Figure 2:
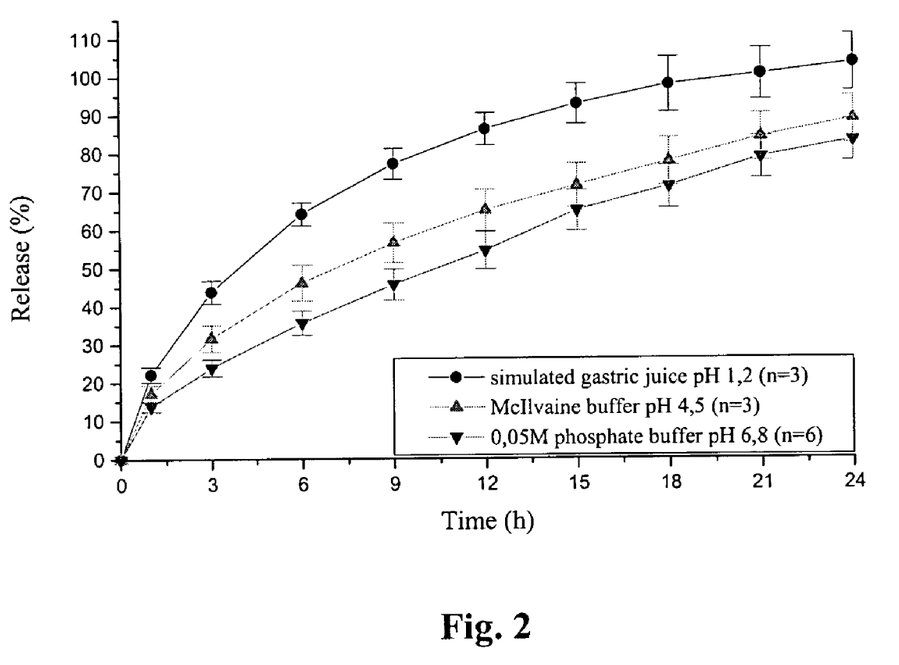
FIG. 2 is a graph illustrating the dissolution profiles of a matrix tablet formulation according to the present invention which contains 4% by weight of CARBOPOL® in 3 different pH media.

FIG. 2 represents a graph illustrating the dissolution profiles of a matrix tablet formulation according to the present invention. The matrix tablet contains 4% by weight CARBOPOL®, the detailed composition is given in Example 2. The release characteristics of the matrix tablet in 3 different pH media are shown, i.e., in 0.05 M phosphate buffer, pH=6.8, n=x, in simulated gastric juice, pH=1.2, n=x, and in McIlvaine buffer, pH=4.5, n=x; (x . . . represents the number of units tested). The value percent of released active ingredient is plotted against the time (hours).

Figure 3:
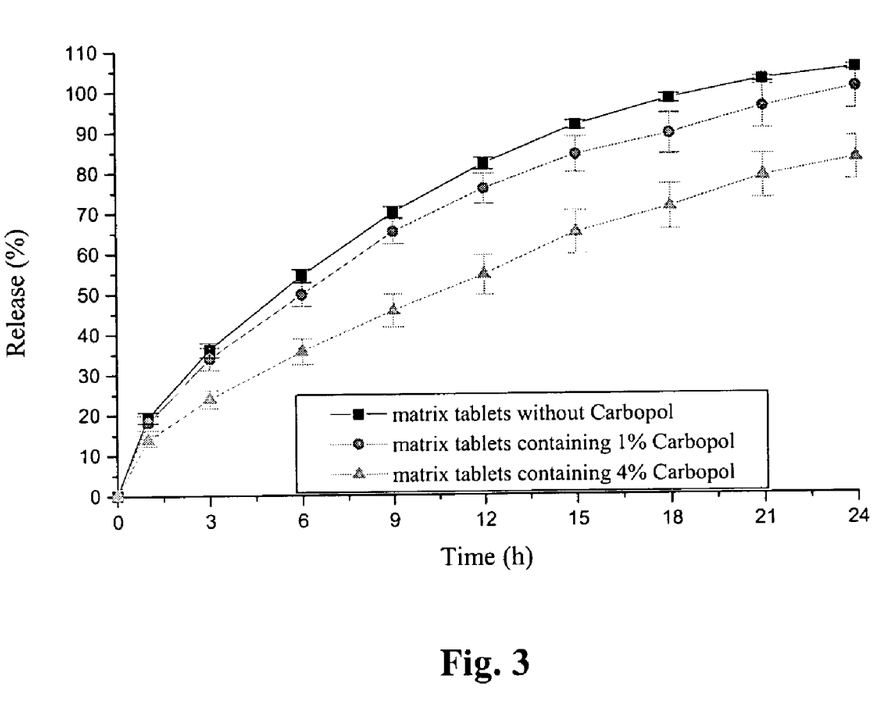
FIG. 3 is a graph illustrating the dissolution profiles of 3 matrix tablet formulations according to the present invention which contain 0%, 1%, and 4% by weight of CARBOPOL®, respectively.

FIG. 3 represents a graph illustrating the dissolution profiles of 3 matrix tablet formulations according to the present invention. The matrix tablets contain no CARBOPOL®, 1% or 4% by weight of CARBOPOL®, respectively, the detailed compositions are given in Examples 1, 2, and 4. The medium is a 0.05 M phosphate buffer, pH=6.8. The value percent of released active ingredient is plotted against the time (hours).

FIGS. 2 and 3 show a pH-independent in vitro release characteristic in the range from pH 1 to 7.5 in case CARBOPOL® is not present and a pH-dependent release characteristic wherein the release characteristic in the range of pH<4.5 is faster in case CARBOPOL® is present. An increase of the amount of CARBOPOL® leads to a decreased releasing rate.

The advantages of the present invention are manifold. According to the present invention, extended release tablets containing pramipexole or its salt are available showing different in vitro release profiles. It is possible to select a tailor-made release characteristic for patient's needs, symptoms, and clinical picture observed.

The primary indication for pramipexole, Parkinson's disease, is an affliction that becomes more prevalent with advancing age and is often accompanied by decline in memory. Therefore, the matrix tablets according to the present invention providing an extended or slow release of pramipexole or a salt thereof allows to simplify the patient's administration scheme by reducing the amount of recommended daily intakes and improves patient's compliance, particularly relevant for elderly patients. The inventive extended release tablet formulation provides a daily dose preferably administered at one time.

Furthermore, the tablets of the present invention may be manufactured via a direct compression, wet or dry granulation process which applies to both types of extended release matrix tablets.

The invention described will now be illustrated by the Examples which follow various other embodiments and will become apparent to the skilled person from the present specification. However, it is expressly pointed out that the Examples and description are intended solely as an illustration and should not be regarded as restricting the invention.

EXAMPLES

According to the present invention pramipexole extended release tablets have been manufactured. The tablets of the Examples are white to off-white, 14×6.8 mm oblong shaped, biconvex tablets. The tablets are intended to be administered orally, and shall not be divided into halves. The pramipexole tablets in the Examples contain 0.75 mg of pramipexole dihydrochloride monohydrate, corresponding to 0.524 mg of pramipexole free, anhydrous base.

Example 1

One embodiment of the qualitative and quantitative composition of pramipexole extended release tablets according to the present invention is shown in Table 1.

TABLE 1

Qualitative and Quantitative Composition of Pramipexole Extended Release Tablet

| Ingredient | mg per 0.75 mg tablet | Function | Reference to Standards |
|---|---|---|---|
| Pramipexole dihydrochloride monohydrate, peg-milled | 0.750 | Active ingredient | Corporate standard |
| Hypromellose 2208 (Methocel K 15M) | 157.500 | Swelling agent | Ph.Eur./USP |
| Corn starch | 183.700 | Filler | Ph.Eur./NF |
| Carbomer 941 (CARBOPOL ® 71 G) | 3.500 | Gelling agent | Ph.Eur./NF |
| Colloidal silicon dioxide | 2.800 | Glidant | Ph.Eur./NF |
| Magnesium stearate | 1.750 | Lubricant | Ph.Eur./NF |
| Total | 350.000 | | |

Example 2

A further embodiment of the qualitative and quantitative composition of pramipexole extended release tablets according to the present invention is shown in Table 2.

TABLE 2

Qualitative and Quantitative Composition of Pramipexole Extended Release Tablet

| Ingredient | mg per 0.75 mg tablet | Function | Reference to Standards |
|---|---|---|---|
| Pramipexole dihydrochloride monohydrate, peg-milled | 0.750 | Active ingredient | Corporate standard |
| Hypromellose 2208 (Methocel K 15M) | 157.500 | Swelling agent | Ph.Eur./USP |
| Corn starch | 174.600 | Filler | Ph.Eur./USP |
| Carbomer 941 (CARBOPOL ® 71 G) | 14.000 | Gelling agent | Ph.Eur./USP |
| Colloidal silicon dioxide | 1.400 | Glidant | Ph.Eur./USP |
| Magnesium stearate | 1.750 | Lubricant | Ph.Eur./USP |
| Total | 350.000 | | |

Example 3

The batch formula for the two pramipexole tablet formulations of Example 1 and 2 is shown in Table 3. The batch size of the final mixture corresponds to a batch size of 2000 tablets.

TABLE 3

Composition per Batch of Pramipexole 0.75 mg ER Tablets

| Ingredient | Grams per batch Example 1 | Grams per batch Example 2 |
|---|---|---|
| Pramipexole dihydrochloride monohydrate, peg-milled | 1.500 | 1.500 |
| Hypromellose 2208 | 315.000 | 315.000 |
| Corn starch | 367.400 | 349.200 |
| Carbomer 941 | 7.000 | 28.000 |
| Colloidal silicon dioxide | 5.600 | 2.800 |
| Magnesium stearate | 3.500 | 3.500 |
| Total Mass | 700.000 | 700.000 |

Example 4

The following Example shows a pramipexole tablet formulation which corresponds to formulation a) providing a release characteristic independent in the pH range of 1 to 7.5.

TABLE 4

| Constituents | mg/tablet |
|---|---|
| Pramipexole-dihydrochloride monohydrate, peg-milled | 0.750 |
| Hypromellose 2208 (Methocel K 100M) | 157.500 |

TABLE 4-continued

| Constituents | mg/tablet |
| --- | --- |
| Corn starch | 187.900 |
| Colloidal silicon dioxide | 2.100 |
| Magnesium stearate | 1.750 |
| Total weight matrix tablet | 350.000 |

Example 5

The following Examples 6 to 14 show pramipexole tablet formulations which correspond to formulation b) providing a faster release characteristic for pH<4.5.

TABLE 5

| Constituents | mg/tablet |
| --- | --- |
| Pramipexole dihydrochloride monohydrate, peg-milled | 0.750 |
| Hypromellose 2208 (Methocel K 15M) | 175.000 |
| Carboxymethyl cellulose sodium | 87.500 |
| Lactose monohydrate (200 mesh) | 52.500 |
| Microcrystalline cellulose (grade PH 101) | 31.100 |
| Colloidal silicon dioxide | 1.400 |
| Magnesium stearate | 1.750 |
| Total weight matrix tablet | 350.000 |

Example 6

TABLE 6

| Constituents | mg/tablet |
| --- | --- |
| Pramipexole dihydrochloride monohydrate, peg-milled | 0.750 |
| Hypromellose 2208 (Methocel K 15M) | 175.000 |
| Carboxymethyl cellulose sodium | 87.500 |
| Lactose monohydrate (200 mesh) | 52.500 |
| Microcrystalline cellulose (grade PH 101) | 27.600 |
| Carbomer 941 (CARBOPOL ® 71 G) | 3.500 |
| Colloidal silicon dioxide | 1.400 |
| Magnesium stearate | 1.750 |
| Total weight matrix tablet | 350.000 |

Example 7

TABLE 7

| Constituents | mg/tablet |
| --- | --- |
| Pramipexole dihydrochloride monohydrate, peg-milled | 0.750 |
| Hypromellose 2208 (Methocel K 15M) | 175.000 |
| Carboxymethyl cellulose sodium | 87.500 |
| Lactose monohydrate (200 mesh) | 45.500 |
| Microcrystalline cellulose (grade PH 101) | 24.100 |
| Carbomer 941 (CARBOPOL ® 71 G) | 14.000 |
| Colloidal silicon dioxide | 1.400 |
| Magnesium stearate | 1.750 |
| Total weight matrix tablet | 350.000 |

Example 8

TABLE 8

| Constituents | mg/tablet |
| --- | --- |
| Pramipexole dihydrochloride monohydrate, peg-milled | 0.750 |
| Carbomer 941 (CARBOPOL ® 71 G) | 87.500 |
| Lactose monohydrate (200 mesh) | 225.400 |
| Microcrystalline cellulose (grade PH 101) | 33.200 |
| Colloidal silicon dioxide | 1.400 |
| Magnesium stearate | 1.750 |
| Total weight matrix tablet | 350.000 |

Example 9

TABLE 9

| Constituents | mg/tablet |
| --- | --- |
| Pramipexole dihydrochloride monohydrate, peg-milled | 0.750 |
| Carbomer 941 (CARBOPOL ® 71 G) | 70.000 |
| Lactose monohydrate (200 mesh) | 242.900 |
| Microcrystalline cellulose (grade PH 101) | 33.200 |
| Colloidal silicon dioxide | 1.400 |
| Magnesium stearate | 1.750 |
| Total weight matrix tablet | 350.000 |

Example 10

TABLE 10

| Constituents | mg/tablet |
| --- | --- |
| Pramipexole dihydrochloride monohydrate, peg-milled | 0.750 |
| Carbomer 941 (CARBOPOL ® 71 G) | 70.000 |
| Lactose monohydrate (200 mesh) | 140.000 |
| Calcium Phosphate, dibasic dihydrate | 136.100 |
| Colloidal silicon dioxide | 1.400 |
| Magnesium stearate | 1.750 |
| Total weight matrix tablet | 350.000 |

Example 11

TABLE 11

| Constituents | mg/tablet |
| --- | --- |
| Pramipexole dihydrochloride monohydrate, peg-milled | 0.750 |
| Carbomer 941 (CARBOPOL ® 71 G) | 52.500 |
| Lactose monohydrate (200 mesh) | 140.000 |
| Calcium Phosphate, dibasic dihydrate | 153.600 |
| Colloidal silicon dioxide | 1.400 |
| Magnesium stearate | 1.750 |
| Total weight matrix tablet | 350.000 |

Example 12

TABLE 12

| Constituents | mg/tablet |
|---|---|
| Pramipexole dihydrochloride monohydrate, peg-milled | 0.750 |
| Hypromellose 2208 (Methocel K 15M) | 157.500 |
| Corn starch | 163.400 |
| Carbomer 941 (CARBOPOL ® 71 G) | 24.500 |
| Colloidal silicon dioxide | 2.100 |
| Magnesium stearate | 1.750 |
| Total weight matrix tablet | 350.000 |

Example 13

TABLE 13

| Constituents | mg/tablet |
|---|---|
| Pramipexole dihydrochloride monohydrate, peg-milled | 0.750 |
| Hypromellose 2910 (Methocel E 5) | 0.788 |
| Corn starch | 173.812 |
| Hypromellose 2208 (Methocel K 15M) | 157.500 |
| Carbomer 941 (CARBOPOL ® 71 G) | 14.000 |
| Colloidal silicon dioxide | 1.400 |
| Magnesium stearate | 1.750 |
| Total weight matrix tablet | 350.000 |

Example 14

TABLE 14

| Constituents | mg/tablet |
|---|---|
| Pramipexole dihydrochloride monohydrate, peg-milled | 0.750 |
| Hypromellose 2208 (Methocel K 15M) | 148.500 |
| Corn starch | 160.620 |
| Carbomer 941 (CARBOPOL ® 71 G) | 16.500 |
| Colloidal silicon dioxide | 1.980 |
| Magnesium stearate | 1.650 |
| Total weight matrix tablet | 330.000 |

We claim:

1. An extended release tablet formulation comprising pramipexole or a pharmaceutically acceptable salt thereof in a matrix comprising at least two water swelling hydrophilic polymers other than pregelatinized starch, and wherein at least one of the at least two polymers is an anionic polymer and the other is a substantially neutral polymer, and wherein the formulation does not contain pregelatinized starch, the resulting tablet formulation providing a pH-dependent release rate in the range of pH<4.5, and a pH-independent release rate in the range from pH 4.5 to 7.5, wherein the release rate in the range of pH<4.5 is higher than the release rate in the range from pH 4.5 to 7.5, when the formulation is tested in the following pH media: simulated gastric juice at pH 1.2, McIlvaine buffer at pH 4.5 and phosphate buffer at pH 6.8, wherein the content of the anionic polymer is from about 0.5 wt.-% to about 15 wt.-% and the content of the substantially neutral polymer is from about 25 wt.-% to about 65 wt.-%.

2. The extended release tablet formulation according to claim 1, wherein the anionic polymer is selected from the group consisting of optionally crosslinked acrylic acid polymers, and carboxymethyl cellulose.

3. The extended release tablet formulation according to claim 2, wherein the anionic polymer is an optionally crosslinked acrylic acid polymer.

4. The extended release tablet formulation according to claim 3, wherein the anionic polymer is an optionally crosslinked acrylic acid polymer, and wherein the content of the optionally crosslinked acrylic acid polymer in the matrix is from about 1 wt.-% to about 10 wt.-%.

5. The extended release tablet formulation according to claim 1, wherein the substantially neutral polymer is hydroxypropyl cellulose or hydroxypropyl methyl cellulose.

6. The extended release tablet formulation according to claim 5, wherein the substantially neutral polymer is hydroxypropyl methyl cellulose.

7. The extended release tablet formulation according to claim 1, wherein the matrix comprises about:
   (a) 0.05 to 5 wt.-% of pramipexole or a salt thereof
   (b) 0.5 to 15 wt.-% of anionic water swelling polymer(s);
   (c) 25 to 65 wt.-% of neutral water swelling polymer(s); and
   (d) to 100 wt.-% of further excipients.

8. The extended release tablet formulation of claim 1, consisting of pramipexole dihydrochloride monohydrate, hypromellose 2208, corn starch, Carbomer 941, colloidal silicon dioxide, and magnesium stearate.

9. An extended release tablet formulation, according to claim 1, wherein the contained amount of pramipexole or pharmaceutically acceptable salt thereof is sufficient to provide a daily dose administered at one time.

10. A method of manufacturing an extended release tablet formulation comprising pramipexole or a pharmaceutically acceptable salt thereof in a matrix comprising at least two water swelling hydrophilic polymers other than pregelatinized starch, and wherein at least one of the at least two polymers is an anionic polymer and the other is a substantially neutral polymer, and wherein the formulation does not contain pregelatinized starch, the resulting tablet formulation providing a pH-dependent release rate in the range of pH<4.5, and a pH-independent release rate in the range from pH 4.5 to 7.5, wherein the release rate in the range of pH<4.5 is higher than the release rate in the range from pH 4.5 to 7.5, when the formulation is tested in the following pH media: simulated gastric juice at pH 1.2, McIlvaine buffer at pH 4.5 and phosphate buffer at pH 6.8, wherein the content of the anionic polymer is from about 0.5 wt.-% to about 15 wt.-% and the content of the substantially neutral polymer is from about 25 wt.-% to about 65 wt.-% by a direct compression process comprising the steps of:

(1) producing an active ingredient trituration wherein the active ingredient is pramipexole or a pharmaceutically acceptable salt thereof by preblending it with a portion of water swelling polymer(s) and/or excipient(s) in a mixer, wherein pramipexole or the pharmaceutically acceptable salt thereof is milled prior to use;

(2) premixing the active ingredient trituration of step (1), the main portion of the water swelling polymer(s) and/or excipients in a mixer to obtain a pre-mixture;

(3) optionally dry screening the pre-mixture through a screen in order to segregate cohesive particles and to improve content uniformity;

(4) mixing the pre-mixture of step (2) or (3) in a mixer, optionally by adding remaining excipients to the mixture and continuing mixing; and (5) tabletting the final mixture by compressing it on a suitable tablet press to produce matrix tablets.

11. The method according to claim 10, wherein the pramipexole or the pharmaceutically acceptable salt thereof is peg-milled prior to use in step (1).

12. A method of manufacturing an extended release tablet formulation comprising pramipexole or a pharmaceutically acceptable salt thereof in a matrix comprising at least two water swelling hydrophilic polymers other than pregelatinized starch, and wherein at least one of the at least two polymers is an anionic polymer and the other is a substantially neutral polymer, and wherein the formulation does not contain pregelatinized starch, the resulting tablet formulation providing a pH-dependent release rate in the range of pH<4.5, and a pH-independent release rate in the range from pH 4.5 to 7.5, wherein the release rate in the range of pH<4.5 is higher than the release rate in the range from pH 4.5 to 7.5, when the formulation is tested in the following pH media: simulated gastric juice at pH 1.2, McIlvaine buffer at pH 4.5 and phosphate buffer at pH 6.8, wherein the content of the anionic polymer is from about 0.5 wt.-% to about 15 wt.-% and the content of the substantially neutral polymer is from about 25 wt.-% to about 65 wt.-% by a wet granulation process comprising the steps of:

(1) producing an active ingredient trituration wherein the active ingredient is pramipexole or a pharmaceutically acceptable salt thereof by blending it with a portion of the excipients in a mixer, wherein pramipexole or the pharmaceutically acceptable salt thereof is milled prior to use;

(2) granulating the active ingredient trituration of step (1) by adding the granulation liquid;

(3) drying the granules of step (2) in a fluidized bed dryer or a drying oven;

(4) mixing the dried granules of step (3) with the water swelling polymer(s) and/or excipients in a mixer to obtain the final mixture; and (5) tabletting the final mixture of step (4) by compressing it on a suitable tablet press to produce matrix tablets.

13. The method according to claim 12, wherein the pramipexole or the pharmaceutically acceptable salt thereof is peg-milled prior to use in step (1).

14. The method according to claim 12, wherein the granulation liquid of step (2) is water.

15. A method of manufacturing an extended release tablet formulation comprising pramipexole or a pharmaceutically acceptable salt thereof in a matrix comprising at least two water swelling hydrophilic polymers other than pregelatinized starch, and wherein at least one of the at least two polymers is an anionic polymer and the other is a substantially neutral polymer, and wherein the formulation does not contain pregelatinized starch, the resulting tablet formulation providing a pH-dependent release rate in the range of pH<4.5, and a pH-independent release rate in the range from pH 4.5 to 7.5, wherein the release rate in the range of pH<4.5 is higher than the release rate in the range from pH 4.5 to 7.5, when the formulation is tested in the following pH media: simulated gastric juice at pH 1.2, McIlvaine buffer at pH 4.5 and phosphate buffer at pH 6.8, wherein the content of the anionic polymer is from about 0.5 wt.-% to about 15 wt.-% and the content of the substantially neutral polymer is from about 25 wt.-% to about 65 wt.-% by a dry granulation process comprising the steps of:

(1) mixing the active ingredient pramipexole or a pharmaceutically acceptable salt thereof with either a portion of the fillers or all the excipients in a mixer, wherein pramipexole or the pharmaceutically acceptable salt thereof is milled prior to use;

(2) compaction of the mixture of step (1) on a suitable roller compactor;

(3) reducing the ribbons obtained during step (1) to small granules by suitable milling or sieving steps;

(4) optionally mixing the granules of step (3) with the remaining excipients in a mixer to obtain the final mixture; and (5) tabletting the granules of step (3) or the final mixture of step (4) by compressing it on a suitable tablet press to produce matrix tablets.

16. The method according to claim 15, wherein the pramipexole or the pharmaceutically acceptable salt thereof is peg-milled prior to use in step (1).

17. The extended release tablet formulation according to claim 1, wherein the formulation does not have a coating.

18. The extended release tablet formulation according to claim 1, wherein the formulation has a non-functional coating as the only coating.

19. The extended release tablet formulation according to claim 1, consisting of:
(a) 0.1 to 2% by weight of pramipexole or a salt thereof;
(b) 25 to 65% by weight of hydroxypropyl methyl cellulose;
(c) 0 to 40% by weight of carboxymethyl cellulose sodium;
(d) 0 to 75% by weight of corn starch;
(e) 0.5 to 15% by weight of acrylic polymerisate; and
(f) 0.5 to 50% by weight of excipients.

20. The extended release tablet formulation according to claim 1, consisting of:
(a) 0.1 to 2% by weight of pramipexole or a salt thereof;
(b) 25 to 65% by weight of hydroxypropyl methyl cellulose;
(c) 0 to 40% by weight of carboxymethyl cellulose sodium;
(d) 0 to 75% by weight of corn starch;
(e) 0.5 to 15% by weight of acrylic polymerisate;
(f) 0.5 to 50% by weight of excipients; and
(g) optionally a non-functional coating as the only coating.

21. The extended release tablet formulation according to claim 19, wherein the acrylic polymerisate is carbomer 941.

22. The extended release tablet formulation according to claim 19, wherein the excipients are selected from one or more of the following: colloidal silicon dioxide, magnesium stearate, lactose monohydrate, mannitol, microcrystalline cellulose, dibasic anhydrous calcium phosphate, hydroxypropyl cellulose, povidone, copovidone, talc, macrogols, sodium dodecylsulfate, iron oxides, and titanium dioxide.

23. The extended release tablet formulation according to claim 19, wherein the acrylic polymerisate is carbomer 941 and the excipients are selected from one or more of the following: colloidal silicon dioxide, magnesium stearate, lactose monohydrate, mannitol, microcrystalline cellulose, dibasic anhydrous calcium phosphate, hydroxypropyl cellulose, povidone, copovidone, talc, macrogols, sodium dodecylsulfate, iron oxides, and titanium dioxide.

24. The extended release tablet formulation according to claim 20, wherein the acrylic polymerisate is carbomer 941.

25. The extended release tablet formulation according to claim 20, wherein the excipients are selected from one or more of the following: colloidal silicon dioxide, magnesium stearate, lactose monohydrate, mannitol, microcrystalline cellulose, dibasic anhydrous calcium phosphate, hydroxypropyl cellulose, povidone, copovidone, talc, macrogols, sodium dodecylsulfate, iron oxides, and titanium dioxide.

26. The extended release tablet formulation according to claim 20, wherein the acrylic polymerisate is carbomer 941 and the excipients are selected from one or more of the following: colloidal silicon dioxide, magnesium stearate, lactose monohydrate, mannitol, microcrystalline cellulose, dibasic anhydrous calcium phosphate, hydroxypropyl cellulose, povidone, copovidone, talc, macrogols, sodium dodecylsulfate, iron oxides, and titanium dioxide.

27. An extended release tablet formulation comprising pramipexole or a pharmaceutically acceptable salt thereof in a matrix comprising:
  at least one water swelling hydrophilic anionic polymer, at least one water swelling hydrophilic substantially neutral polymer and optionally excipients, the resulting tablet providing a pH-dependent release rate in the range of pH<4.5, and a pH-independent release rate in the range from pH 4.5 to 7.5, wherein the release rate in the range of pH<4.5 is higher than the release rate in the range from pH 4.5 to 7.5, when the formulation is tested in the following pH media: simulated gastric juice at pH 1.2, McIlvaine buffer at pH 4.5 and phosphate buffer at pH 6.8, wherein the content of anionic polymer in the matrix is from about 0.5 to 15 wt.-% and wherein the content of the neutral polymer in the matrix is from about 25 wt.-% to about 65 wt.-%, wherein said tablet either does not have a coating or has a non-functional coating as the only coating and wherein the formulation does not contain pregelatinized starch.

28. The extended release tablet formulation according to claim 6, wherein the content of hydroxypropyl methyl cellulose in the matrix is from about 35 wt.-% to about 55 wt. %.

29. The extended release tablet formulation according to claim 1, wherein the content of pramipexole or a pharmaceutically acceptable salt thereof is from about 0.05 wt.-% to about 5 wt.-%.

30. The extended release tablet formulation according to claim 1, wherein the content of pramipexole or a pharmaceutically acceptable salt thereof is from about 0.1 mg to about 10 mg.

31. The extended release tablet formulation according to claim 1, wherein the content of pramipexole or a pharmaceutically acceptable salt thereof is from about 0.1 mg to about 5 mg.

* * * * *

UNITED STATES PATENT AND TRADEMARK OFFICE
CERTIFICATE OF CORRECTION

| | | |
|---|---|---|
| PATENT NO. | : 7,695,734 B2 | Page 1 of 1 |
| APPLICATION NO. | : 11/202713 | |
| DATED | : April 13, 2010 | |
| INVENTOR(S) | : Thomas Friedl et al. | |

It is certified that error appears in the above-identified patent and that said Letters Patent is hereby corrected as shown below:

Column 18, line 21 should read:
(a) 0.05 to 5 wt.-% of pramipexole or a salt thereof;

Column 22, line 2 should read:
...is from about 0.5 wt.-% to about 15 wt.-% and wherein the content of...

Column 22, line 10 should read:
...lose in the matrix is from about 35 wt.-% to about 55 wt.-%.

Signed and Sealed this
Twenty-sixth Day of June, 2012

David J. Kappos
*Director of the United States Patent and Trademark Office*